(12) United States Patent
Coope et al.

(10) Patent No.: US 9,952,176 B2
(45) Date of Patent: Apr. 24, 2018

(54) AUTOMATED SIZE SELECTION OF NUCLEIC ACIDS

(75) Inventors: Robin J. Noel Coope, Vancouver (CA); Jared Raymond Slobodan, Vancouver (CA)

(73) Assignee: British Columbia Cancer Agency Branch, Vancouver (CA)

(*) Notice: Subject to any disclaimer, the term of this patent is extended or adjusted under 35 U.S.C. 154(b) by 867 days.

(21) Appl. No.: 14/123,897

(22) PCT Filed: Jun. 15, 2012

(86) PCT No.: PCT/CA2012/050404
§ 371 (c)(1),
(2), (4) Date: Mar. 31, 2014

(87) PCT Pub. No.: WO2012/171127
PCT Pub. Date: Dec. 20, 2012

(65) Prior Publication Data
US 2014/0202859 A1    Jul. 24, 2014

Related U.S. Application Data

(60) Provisional application No. 61/497,586, filed on Jun. 16, 2011.

(51) Int. Cl.
*G01N 27/447* (2006.01)

(52) U.S. Cl.
CPC . *G01N 27/44721* (2013.01); *G01N 27/44739* (2013.01)

(58) Field of Classification Search
CPC .................. G01N 27/44721; G01N 27/44739
See application file for complete search history.

(56) References Cited

U.S. PATENT DOCUMENTS

| 4,624,769 | A | | 11/1986 | Simada et al. |
| 4,935,357 | A | * | 6/1990 | Szybalski ............... C12N 9/22 435/199 |

(Continued)

FOREIGN PATENT DOCUMENTS

| CN | 1695775 A | | 11/2005 | |
| JP | 62-182657 | * | 11/1987 | ............. G01N 33/50 |

(Continued)

OTHER PUBLICATIONS

"Pippin Prep: DNA size selection system, Operations Manual", (V 4.7), Sage Science, May 25, 2012, pp. 4.1-4.3, 6.1-6.5, and 10.1-10.2.

(Continued)

*Primary Examiner* — Luan V Van
*Assistant Examiner* — Steven E Rosenwald
(74) *Attorney, Agent, or Firm* — Oyen Wiggs Green & Mutala LLP

(57) ABSTRACT

Apparatus and methods for size selecting nucleic acid molecules having wide range of applications including the production of DNA libraries for sequencing technologies. An automated high throughput system for size selection of multiple nucleic acid samples that uses imaging technique to detect the progress of a target fraction and feedback from the imaging to control electrophoresis. Predictive algorithms for timed nucleic acid extractions are generated to provide size selected nucleic acid molecules of required size ranges.

40 Claims, 12 Drawing Sheets

(56) References Cited

U.S. PATENT DOCUMENTS

| | | | |
|---|---|---|---|
| 5,288,465 A | 2/1994 | Margolis | |
| 5,538,614 A * | 7/1996 | Han | G01N 27/4473 204/456 |
| 5,587,062 A * | 12/1996 | Togawa | G01N 27/44739 204/456 |
| 5,635,045 A * | 6/1997 | Alam | G01N 27/4473 204/456 |
| 6,064,754 A * | 5/2000 | Parekh | G01N 27/44704 382/129 |
| 6,146,511 A * | 11/2000 | Slater | G01N 27/447 204/457 |
| 6,198,107 B1 | 3/2001 | Seville | |
| 6,387,235 B1 | 5/2002 | Irie et al. | |
| 6,496,309 B1 * | 12/2002 | Bliton | G02B 13/24 359/368 |
| 6,512,236 B2 | 1/2003 | Seville | |
| 6,627,446 B1 * | 9/2003 | Roach | G01N 27/44743 204/451 |
| 6,793,790 B1 * | 9/2004 | Olivares | G01N 27/44717 204/461 |
| 6,914,250 B2 | 7/2005 | Seville | |
| 7,678,254 B2 * | 3/2010 | Hanafusa | G01N 27/44743 204/451 |
| 2004/0079639 A1 * | 4/2004 | Adachi | G01N 27/44717 204/451 |
| 2006/0201807 A1 | 9/2006 | Sobek et al. | |
| 2008/0142365 A1 * | 6/2008 | Kober | G01N 27/44726 204/450 |
| 2010/0126862 A1 * | 5/2010 | Sabin | G01N 27/447 204/457 |

FOREIGN PATENT DOCUMENTS

| | | |
|---|---|---|
| JP | 0708833 A | 9/1995 |
| JP | 2000-088803 A | 3/2000 |
| JP | 2004-144532 A | 5/2004 |
| JP | 2004-155687 A | 6/2004 |
| JP | 2004-290109 A | 10/2004 |
| JP | 2006-509996 A | 3/2006 |
| JP | 2007-163186 A | 6/2007 |
| JP | 2010-502962 A | 1/2010 |
| WO | 9316788 A1 | 9/1993 |
| WO | 9325896 A1 | 12/1993 |
| WO | 9922228 A1 | 5/1999 |
| WO | 0150121 A2 | 7/2001 |
| WO | 03084629 A2 | 10/2003 |
| WO | 2008006201 A1 | 1/2008 |
| WO | 2008028127 A1 | 3/2008 |
| WO | 2012024658 A2 | 2/2012 |

OTHER PUBLICATIONS

Cox, J. et al., "Automated Selection of Anti-Protein Aptamers", Bioorganic and Medicinal Chemistry, Oct. 1, 2001, vol. 9(10), pp. 2525-2531.

Slobodan, J. et al., "A 96 Channel Size Selection Robot", poster, AGBT 2010, Marco Island, Florida, Feb. 2010.

Berezovski, M. et al., "Nonequilibrium Capillary Electrophoresis of Equilibrium Mixtures: A Universal Tool for Development of Aptamers", JAAS 2005, 127, pp. 3165-3171.

Drabovich, A. et al., "Selection of Smart Aptamers by Equilibrium Capillary Electrophoresis of Equilibrium Mixers (ECEEM)", JAAS, 2005, 127, pp. 11224-11225.

Li, G. et al., "Design, simulation, and optimization of a miniaturized device for size-fractioned DNA extraction", Electrophoresis 2007, 28, pp. 4661-4667.

"LabChip XT/XTe Advanced Nucleic Acid Size Selection and Collection", brochure, Caliper LifeSciences, Apr. 2011.

Lin, R. et al., "Selective extraction of size-fractioned DNA samples in microfabricated electrophoresis devices", Journal of Chromatography A, vol. 1010, No. 2, pp. 255-268, 2003.

Gobel, U. et al., "Quantitative electroelution of oligonucleotides and large DNA fragments from gels and purification by electrodialysis", Journal of Biochemical and Biophysical Methods, vol. 14, No. 5, pp. 245-260, 1987.

Li, G. et al., "Design of a PMMA Chip for Selective Extraction of Size-Fractioned DNA", Conference on Nano/Micro Engineered and Molecular Systems, pp. 105-109, 2006.

* cited by examiner

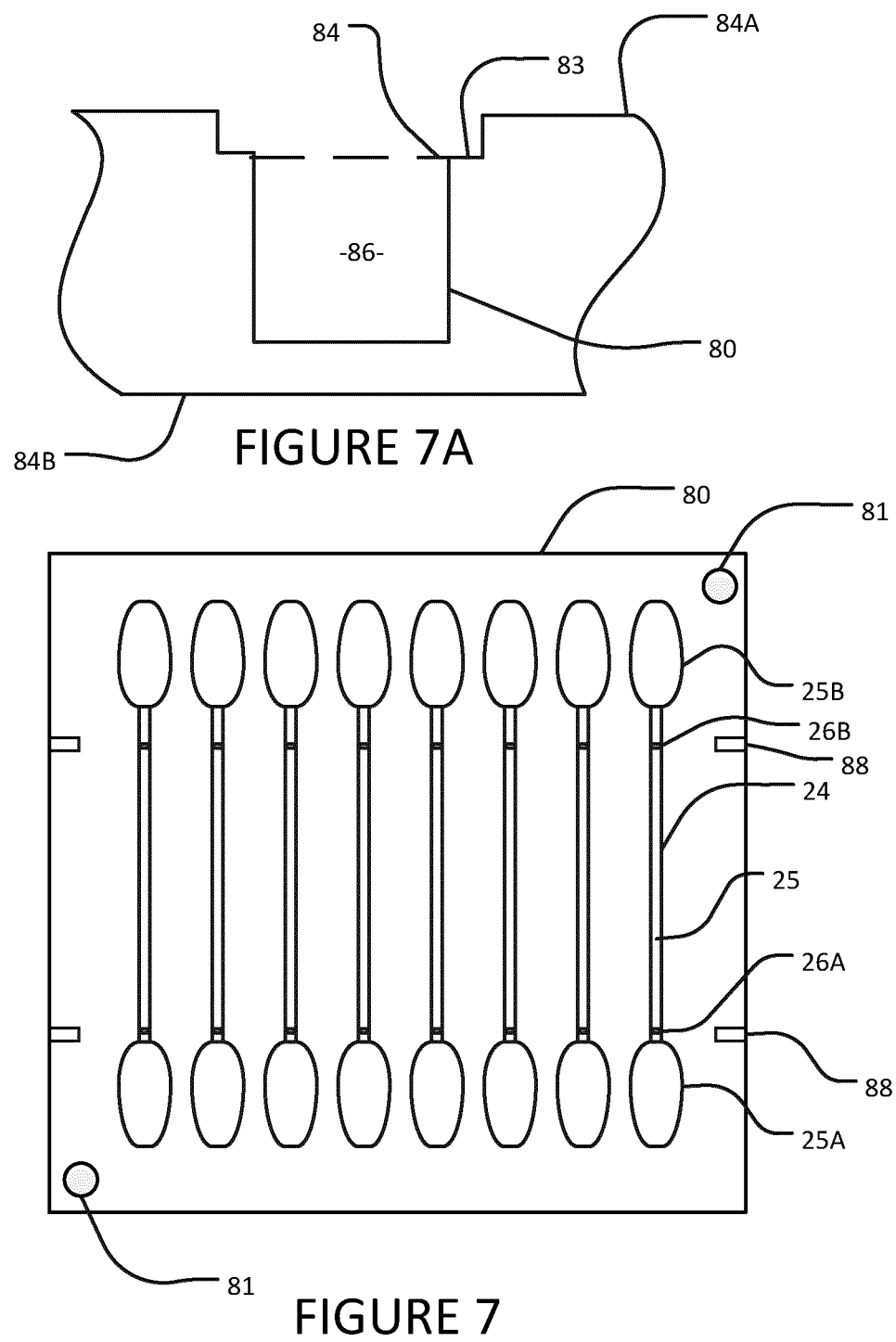

AUTOMATED SIZE SELECTION OF NUCLEIC ACIDS

REFERENCE TO RELATED APPLICATION

This application claims Paris convention priority from U.S. application No. 61/497,586 filed on 16 Jun. 2011 and entitled Method and Apparatus for Automated Size Selection of Nucleic Acids which is hereby incorporated herein by reference for all purposes. For purposes of the United States of America, this application claims the benefit under 35 U.S.C. § 119 of U.S. application No. 61/497,586 filed on 16 Jun. 2011 and entitled Method and Apparatus for Automated Size Selection of Nucleic Acids which is hereby incorporated herein by reference for all purposes.

TECHNICAL FIELD

This invention relates to the automated size selection of nucleic acids. Aspects of the invention provide methods and apparatus useful for selecting nucleic acids according to size.

BACKGROUND

There are a wide range of applications in which it is desirable to select nucleic acids, such as DNA or RNA by size. For example, size selection is used in the production of DNA libraries for use in sequencing and other applications.

Various techniques for DNA size selection exist. Some of these techniques are undesirably labour intensive. One method for DNA size selection is to perform electrophoresis of a sample containing DNA in a gel. Since DNA of different sizes have different mobilities in the gel the electrophoresis separates the DNA into different bands by size. A band containing DNA in the desired size range can be identified and then manually cut out from the gel. The desired DNA can then be extracted from the gel.

Some electrophoresis systems comprise wells formed in a gel. DNA can be run into the wells by electrophoresis. Invitrogen E-gels and the Lonza Flash Gel™ provide such wells.

Y-channel size selection machines are another technology for DNA size selection. Examples are the Sage Pippin Prep™ and the Caliper XT™ machines. These machines can extract DNA of a desired size range from a sample by diverting DNA of the desired size range into a side channel and collecting the diverted DNA against a molecular weight cut-off filter.

Solid Phase Reversible Immobilization Beads (SPRI) beads which are available from Beckman Coulter and others may be used to trap DNA of a certain size and then release the DNA after a wash and a change in pH.

There remains a need for a DNA size-selection technology that can provide high throughput. There remains a need for a DNA size-selection technology that can provide accurate DNA size selection with reduced labour.

SUMMARY

This invention has a number of aspects that may be applied together. Some of the aspects have independent application. One aspect provides apparatus for automated size-selection of nucleic acids. Another aspect provides a computer system for controlling apparatus for automated size-selection of nucleic acids. Another aspect provides methods for automated size-selection of nucleic acids. The nucleic acids may comprise DNA and/or RNA. Another aspect provides cartridges useful inter alia for automated size selection of nucleic acids.

In one example embodiment, nucleic acids are size selected by loading DNA samples individually into agarose channels, each of which has a loading well at one end of the channel and an extraction well downstream. Electrophoresis is performed on the nucleic acids after loading and the nucleic acids are separated by size as they migrate towards the extraction well. The channel is imaged at regular intervals during this process and a software algorithm uses the images to identify reference bands and predict the time at which the desired nucleic acid fragments will arrive at the extraction well. The channel current is also individually controllable via pulse width modulation of the DC voltage so that if adjacent samples are running at different speeds, the extractions times can be altered so that no two samples need to be extracted at the same moment.

Another aspect of the invention provides methods for size-selection of nucleic acids such as DNA, RNA and the like. Such methods comprise moving nucleic acids from a sample along a channel by electrophoresis; automatically monitoring progress of a reference fraction of the nucleic acids along the channel; based on the monitoring, estimating an estimated time of arrival of a target fraction of the nucleic acids at an extraction well in the channel; and extracting fluid containing the target fraction from the extraction well at the estimated time of arrival. The reference fraction may be the same as or different from the target fraction. For example, in some embodiments the reference fraction may comprise nucleic acids that are abundant in the sample (either originally present in the sample or added to the sample as a size marker) and the target fraction may comprise nucleic acids having sizes different from that of the reference fraction. Progress of the target fraction along the channel may be inferred from progress of the reference fraction. For example, the target fraction may be known to lead or lag behind the reference fraction by a certain percentage. In some embodiments, the target fraction of the nucleic acids comprises an adapter joined to a nucleic acid molecule of interest, and the reference fraction of the nucleic acids comprise the adapter which is not joined to the nucleic acid molecule of interest. In some embodiments, the methods may comprise automatically monitoring progress of a plurality of reference fractions of the nucleic acids along the channel. The plurality of reference fractions may comprise a DNA or RNA ladder of known sizes.

In some embodiments the monitoring comprises, at spaced apart times, obtaining images of the channel and identifying areas in the images corresponding to the reference fraction. The images may, for example, be acquired by a camera mounted to view the channel. The camera may image a large number of channels simultaneously. Progress of the reference fractions (which are not necessarily the same for different channels) in multiple channels may be monitored using the same set of images. The estimated time of arrival of the target fraction may be estimated in some cases based on an average velocity of the target fraction based on differences between the positions of the reference fraction in two or more of the images. The images may comprise high dynamic range images. For example, the images may be obtained using a high dynamic range sensor or may be assembled from two or more different exposures. In some embodiments the images have a bit-depth of 10-bits or 12-bits or more. In some embodiments obtaining each of the images comprises operating an imaging device to obtain a plurality of different exposures of the channel and combining the plurality of different exposures to yield the image, wherein the image has a greater dynamic range than any of the plurality of different exposures.

Some embodiments comprise specifying a size or size range of the target fraction. For example, the size or size range of the target fraction may be specified in absolute terms or relative to one or more of the reference fractions. For example, the size or size range of the target fraction may be specified as leading or lagging behind the reference fraction by a certain percentage. Some embodiments comprise scheduling a time of arrival for the target fraction at the extraction well; comparing the scheduled time of arrival to the estimated time of arrival and adjusting one or more electrophoresis parameters of an electrophoresis signal based on any difference between the scheduled time of arrival and the estimated time of arrival. In such embodiments, target fractions in different channels may be caused to arrive at extraction wells at different times (facilitating extraction of the target fractions using a single mechanism such as a robot carrying a pipetter that services each channel at the scheduled time). Also in such embodiments target fractions in different channels may be caused to arrive at extraction wells at the same time (facilitating extraction of the target fractions using a multi-channel mechanism such as a robot carrying a multi-channel pipetter that services several channels simultaneously at the scheduled time).

Adjusting the one or more electrophoresis parameters may comprise adjusting a duty cycle of the electrophoresis signal, adjusting potentials of the electrophoresis signal or adjusting other parameters that define the electrophoresis signal.

In some embodiments the method determines a location of an extraction well and/or a loading well in one or more channels by image analysis. This facilitates systems in which extraction wells in different channels are at different locations and also facilitates automatic compensation for variations in the positions of extraction wells and/or loading wells.

Another aspect of the invention provides apparatus for size-selection of nucleic acids. The apparatus comprises: a channel having first and second ends and an extraction well in the channel; an electrophoresis power supply connected to deliver an electrophoresis signal to the channel to move nucleic acids from a sample along the channel; an imaging device mounted to image the channel; a controller connected to obtain images from the imaging device. the controller is configured to: automatically monitor progress of a reference fraction of the nucleic acids along the channel by analysis of the images; based on the monitoring, estimate an estimated time of arrival of a target fraction of the nucleic acids at the extraction well in the channel; and operate a mechanism to extract fluid containing the target fraction from the extraction well at the estimated time of arrival.

The imaging device may comprise an electronic camera. The camera may be equipped with a filter that attenuates light outside of an emission band of a dye associated with the nucleic acid.

In some embodiments the mechanism comprises a robotic system comprising a pipetter operable to transfer a sample into a loading well in the channel and to extract the fluid from the extraction well. In some embodiments the pipetter comprises a multi-channel pipetter capable of simultaneously introducing multiple samples into multiple channels or simultaneously extracting fluids from extraction wells in multiple channels.

In some embodiments the channel comprises an elongated groove having opposed first and second sides and an electrophoresis medium in the groove and the first and second sides having steps extending longitudinally along the first and second sides, the electrophoresis medium filling the groove up to the steps.

The electrophoresis medium may comprise, for example, a gel such as an agarose gel, an acrylamide gel, a denaturing acrylamide gel, or the like.

In some embodiments the controller is configured to determine a location of the extraction well in the channel by image analysis of one or more of the images and to move the pipette tip to the determined location of the extraction well.

In some embodiments the controller is configured to compare the estimated time of arrival of the target fraction at the extraction well to a desired time of arrival of the target fraction at the extraction well and to control the electrophoresis power supply to adjust one or more electrophoresis parameters of the electrophoresis signal based on any difference between the desired time of arrival and the estimated time of arrival.

In some embodiments the controller is configured to control a rate of movement of the nucleic acids along the channel by proportional feedback control of the one or more electrophoresis parameters based on an error signal comprising a difference between the estimated time of arrival and a desired time of arrival of the target fraction at the extraction well.

In some embodiments the controller comprises a scheduler configured to generate the desired time of arrival of the target fraction at the extraction well.

The apparatus may comprise a proportional feedback controller configured to control the electrophoresis power supply to vary an average speed of the target fraction along the channel in response to an error signal representing a difference between the estimated time of arrival of the target fraction at the extraction well and a desired time of arrival of the target fraction at the extraction well. In some embodiments the controller is configured to reduce a difference between the estimated arrival time and the desired arrival time by temporarily interrupting application of the electrophoresis signal to the channel.

Another aspect of the invention provides a cassette for use in size selection of nucleic acids. The cassette comprises a plate having a channel formed in the plate, the channel comprising an elongated groove having opposed first and second sides and an electrophoresis medium in the groove, first and second sides having steps, the electrophoresis medium filling the groove up to the steps. The plate may have one or more holes, grooves or other features for locking the plate into a known location relative to a robot. The channel may include both a loading well and an extraction well at spaced apart locations along the channel. The plate may optionally be transparent at least in its portion below the channel.

Further aspects of the invention and features of example embodiments of the invention are illustrated in the accompanying drawings and/or described below.

BRIEF DESCRIPTION OF THE DRAWINGS

The accompanying drawings depict non-limiting example embodiments of the invention.

FIG. 7 is a plan view of an example channel plate.

FIG. 7A is a cross section of an individual channel.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

One aspect of the invention provides an automated method for size selection of multiple nucleic acid samples. The method uses imaging in conjunction with predictive algorithms to time extractions and provide size selected nucleic acids of a desired size range. The method can be practiced to advantage in conjunction with automated apparatus comprising one or more electrophoresis channels, a camera which acquires images of the one or more electrophoresis channels and a robot comprising a pipetter for introducing samples into corresponding channels and extracting size-selected nucleic acids from the channels. The channels may be filled, for example, with an agarose gel or an acrylamide gel. The channels may each have a loading well in the channel and an extraction well spaced apart from the loading well along the channel.

The following description explains construction and operation of example embodiments being used to size-select DNA. For example, the DNA may comprise cDNA derived from RNA. The DNA to be size-selected may have a size in the range of 10 bp to 10 kbp. However, the invention may be applied to size-selection of other nucleic acids such as RNA. In some embodiments the nucleic acids comprise sheared nucleic acids.

Figure 1:
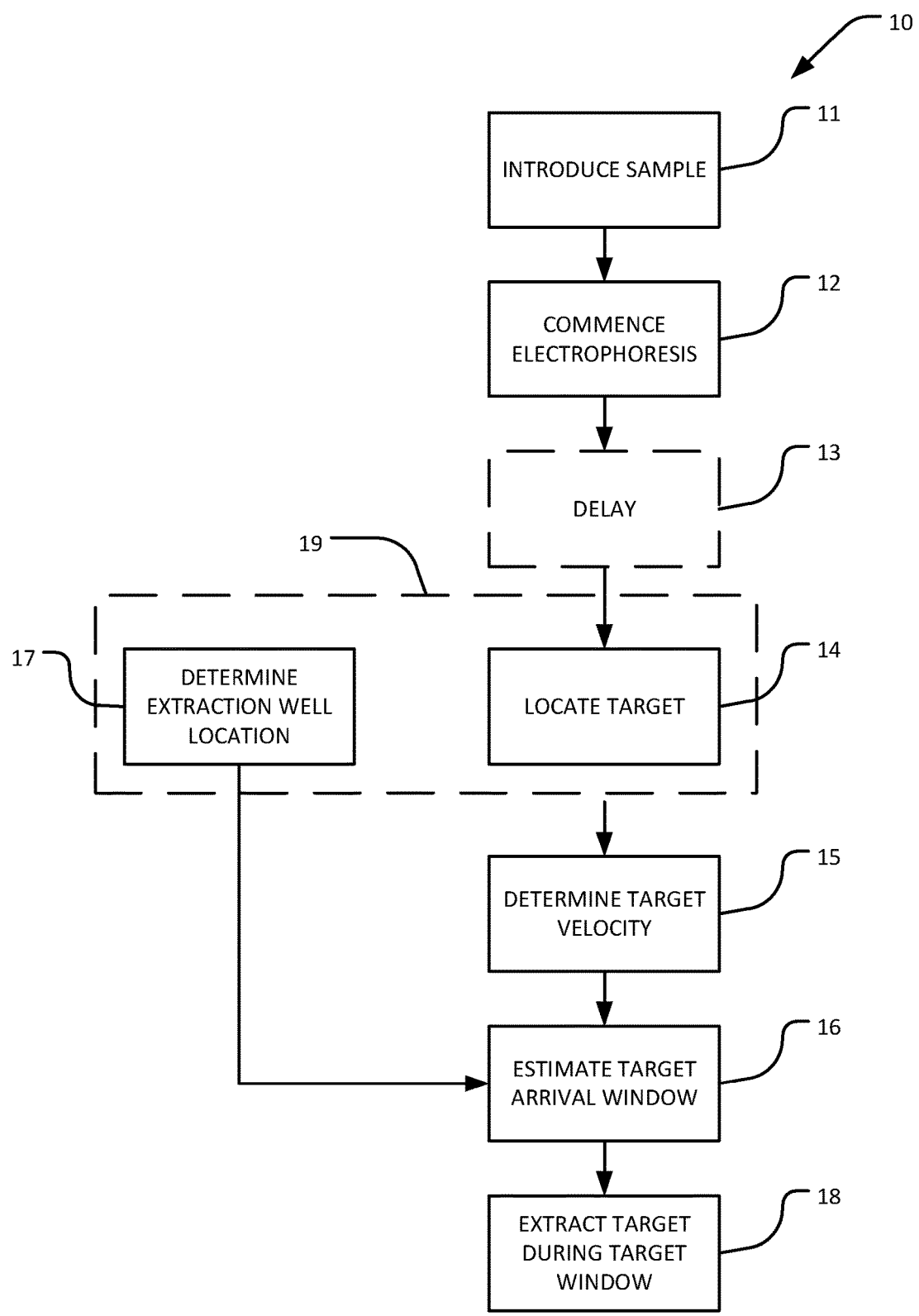
FIG. 1 illustrates a method for size-selecting a nucleic acid according to an example embodiment.

FIG. 1 illustrates a method 10 according to an example embodiment of the invention. In block 11 a sample containing DNA is introduced into a loading well in a channel containing a medium through which the DNA can be moved by electrophoresis. The sample containing the DNA may also comprise a dye (e.g., SYBR Green™ dye or ethidium bromide) which is introduced into the loading well together with the DNA. The function of the dye is to facilitate the detection or imaging of the DNA in the medium. In some embodiments, the DNA molecules in the sample may comprise an adapter, which may be useful for downstream applications such as DNA sequencing. The medium may, for example, comprise an agarose or acrylamide gel. In block 12 electrophoresis is commenced. Electrophoresis may be performed by applying an electrical potential difference between electrodes at opposing ends of the channel. The potential difference may comprise a DC electrical potential, a pulsed DC electrical potential or an unbalanced AC electrical potential, for example. The applied electrical potential drives the DNA to migrate from the loading well along the channel toward an extraction well. DNA of different sizes has different mobilities in the channel and so the DNA becomes size segregated.

Optional block 13 provides a delay to allow the DNA to migrate far enough along the channel that concentrations of DNA of different sizes can be detected. Block 14 comprises determining the location along the channel of target DNA of a desired size range. In some embodiments, block 14 comprises obtaining a sequence of images of the channel with a camera, detecting one or more landmarks in the image(s) corresponding to DNA of one or more known sizes, and determining the position of the target DNA based on the position(s) of the landmark(s). The output of block 14 is a sequence of positions along the channel of the target DNA.

Sizing reference(s) (e.g. landmarks) may be specified at or before run time; whether it is a DNA ladder, or an inherent feature expected to be present in the electropherogram. If the size reference used is a DNA ladder, the DNA ladder may be added to the sample prior to loading the sample into the loading wells. In some embodiments, the size reference is inherently present in the sample. For example, to size-select a cDNA sample derived from miRNA, the sample may comprise both cDNA+adapter fragments (e.g., having a size of 109 bp) as well as adapter-adapter fragments (e.g., having a size of 80 bp). The adapter-adapter fragments may be used as a size reference.

The size-range of the target DNA may be specified in various ways, for example in absolute terms or relative to given reference(s), allowing for excision of fractions with sizes either dependent or independent of the electropherogram profile of the input sample. For example, if the input sample is sheared genomic DNA with an expected peak centre at ~250 bp, the mobility range of the target fraction may be specified relative to the peak centre (e.g. 110%-90% of the peak-centre mobility), or the target may be specified as a absolute size range (e.g. 150 bp-200 bp) independent of the actual mobility of the peak centre.

Block 15 determines an average velocity of the target DNA along the channel. Block 15 may, for example, be as simple as dividing a difference of two positions of the target DNA by an elapsed time between the images from which the positions were determined. Block 15 may take into account more than two positions. For example, block 15 may average or find the median of a plurality of velocities.

Block 16 estimates a time of arrival of the target DNA at the extraction well. This determination may be based on a known, predetermined location of the extraction well. In some embodiments the location of the extraction well is determined in block 17 by locating the image of the extraction well in the images obtained in block 15 (or else separate images obtained for the purpose of locating the extraction well). This image recognition may be model-based (i.e. it is known in advance what the image of a channel is expected to look like in an image, where each channel is expected to be found in the image, and what the image of an extraction well is expected to look like in the image. Locating the extraction well may, for example, comprise, finding a location in the image where the correlation with a model image of an extraction well is maximized. In other simpler embodiments locating the extraction well in the image comprises locating one or more edges corresponding to the extraction well in the image.

For example, the estimated time of arrival may be obtained by adding an estimated travel time to a current time. The estimated travel time may be determined, for example, by dividing a distance between the location of the extraction well and the current location of the target DNA by the current velocity of the target DNA as estimated in block 15.

Block 18 extracts the target DNA from the extraction well at the estimated arrival time. Block 18 may, for example comprise controlling a robot carrying a pipetter to place the pipetter into the extraction well at or before the estimated arrival time and withdrawing fluid from the extraction well into the pipetter at the estimated arrival time. The robot may then dispense the collected fluid into a reservoir where the fluid may be held or delivered for further processing.

Method 10 has a range of variations. In some embodiments information regarding the velocity and/or position of the target DNA is applied to control the velocity of target DNA. Position information obtained from run-time electropherograms and time information is used in a feedback loop to control electrophoresis speed of the target DNA fraction in addition to its arrival time at the extraction well.

Feedback control may be applied, for example, to adjust the estimated arrival time of the target DNA at the extraction well. The estimated arrival time may be adjusted, for example, adjusting a duty cycle and/or voltage of an electrophoresis field and/or by pausing application of the electrophoresis field one or more times. Embodiments which adjust velocity of the target DNA by adjusting duty cycle can be advantageous since the relationship between duty cycle and velocity tends to be linear or nearly linear. This simplifies control. Electrophoresis speed and extraction scheduling may be simultaneously controlled for an arbitrary number of samples. In one embodiment, extraction scheduling processes 96 samples running in parallel.

Figure 1A:
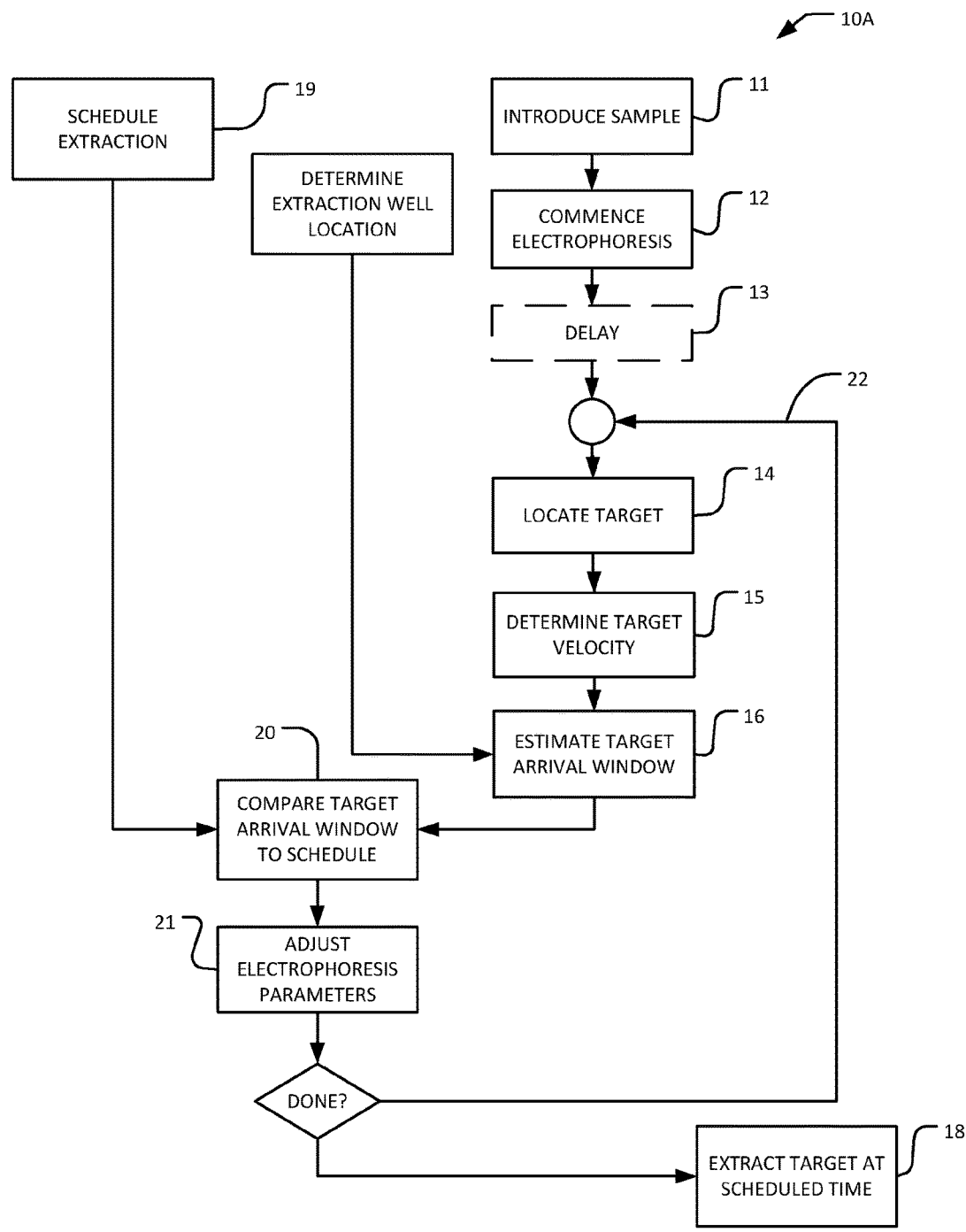
FIG. 1A illustrates an alternative example method.

FIG. 1A illustrates an alternative example method 10A which is similar to method 10 except that it includes a block 19 that schedules a scheduled arrival time for the target DNA and a block 20 that compares the estimated arrival time from block 16 to the scheduled arrival time for the target DNA. Block 21 receives a control signal from block 20 and adjusts electrophoresis parameters based on the control signal. Loop 22 may be repeated periodically at a rate sufficient to control the progress of the target DNA so hat the target DNA arrives at the extraction well at the scheduled time.

In block 21, the electrophoresis parameters may be adjusted, as appropriate, to retard the progress of the target DNA, to accelerate the progress of the target DNA or to maintain the current rate of progress of the target DNA. In some embodiments the adjustment depends merely on the sign of the control signal (i.e. whether the estimated arrival time is before or after the scheduled arrival time). In other embodiments the adjustment is based at least in part on a magnitude of the difference between the estimated arrival time and the scheduled arrival time (or equivalently a magnitude of the difference between an estimated velocity and a velocity that would result in the target DNA arriving at the extraction well at the scheduled time.

In typical cases the target DNA does not have a specific size but has a range of sizes. Thus the target DNA will arrive at an extraction well during a time window having a length determined by the range of sizes in the DNA fraction as well as by the electrophoresis parameters. In some embodiments a target fraction may be specified initially and also continuously adjusted until the fraction is extracted.

Control over the time at which target DNA arrives at an extraction well may be applied to good effect in the case where multiple electrophoresis channels are being operated at the same time. For example, electrophoresis of DNA in each of a plurality of channels may be controlled to cause target DNA in each channel to arrive at an extraction well at a scheduled time such that the scheduled times in different channels are different. The target DNA in different channels may be the same or different. This can facilitate using a robot to extract target DNA from each of the channels without requiring the same pipetter of the robot to be extracting fluid from two extraction wells at the same time. The scheduled times may be assigned to ensure that there is enough time for the robot to make each of the scheduled extractions.

Control over the electrophoresis velocity may be applied to compensate for variations between channels in electrophoresis velocity (caused, for example, by inhomogeneities in the electrophoresis medium or other differences in the electrophoresis medium used in different channels. The control may also be applied to compensate for differences in the location of the extraction well between channels. The control may also be applied to compensate for differences in the target DNA for different channels.

Some embodiments employ a multi-channel robot. For example, such a robot may have a plurality of pipetters arranged so that their tips can be simultaneously inserted into a plurality of extraction wells. For example, the robot may carry 8, 16 or some other number of pipetters. In some such embodiments channels are arranged side-by-side and the robot may be configured to simultaneously introduce fluid into N adjacent loading wells or to simultaneously remove fluid from N adjacent extraction wells.

In some embodiments which use a multi-channel robot, electrophoresis in a plurality of channels is controlled to cause target DNA in the plurality of channels to reach extraction wells at the same scheduled time. The target DNA may differ among the plurality of channels. The robot may then be controlled to place pipette tips into the extraction wells of the plurality of channels at the scheduled time and to simultaneously extract fluid from the extraction wells. Such embodiments permit different scheduled arrival times to be assigned to groups of channels. Electrophoresis in the individual channels in each group may be separately controlled to cause target DNA in each channel in the group to arrive at the corresponding extraction well at the time scheduled for that group. The scheduled times for different groups of channels may be spaced apart such that the robot has time to make the scheduled extractions. Such embodiments can provide high throughput electrophoresis.

The principles described above may also be applied in situations where it is desired to extract two or more fractions from the same sample. For such applications, electrophoresis may be performed to bring a first target fraction to an extraction well and to extract the first target fraction. Subsequently, further electrophoresis may be performed to bring a second fraction to the extraction well. The second fraction may then be extracted. If desired, the first and second target fractions may be kept isolated from one another. For example, each of the first and second target fractions may be transferred from the extraction well to a separate destination well. It is also possible to transfer multiple fractions from the same sample to the same destination well if that is desired.

In some applications, three or more fractions may be extracted from the same sample. Where two or more target fractions are to be extracted from the same sample then extraction of each of the target fractions may be separately scheduled. After a first target fraction has been extracted from a channel at a first scheduled time, electrophoresis parameters for the channel may be controlled to bring the second target fraction to the extraction well for extraction at a second scheduled time.

In some embodiments electrophoresis is controlled in a plurality of channels to bring a corresponding plurality of first target fractions to the extraction wells in the plurality of channels at a first time. A multi-channel pipetter or other multi-channel extraction mechanism may then be applied to transfer the first target fractions to corresponding destination wells. Electrophoresis in the plurality of channels may then be controlled to bring second target fractions to the extraction wells in the channels at the same time. It is not necessary that the spacing between the first target fractions and the second target fractions be the same between the different channels. Electrophoresis may be controlled to move the second target fraction toward the extraction well faster in some channels than in others. In some embodiments electrophoresis is controlled to bring the second target fractions to extraction wells at the same time in the plurality of channels so that the second target fractions can be simultaneously extracted using the multi-channel pipetter.

Figures 2, 2A:
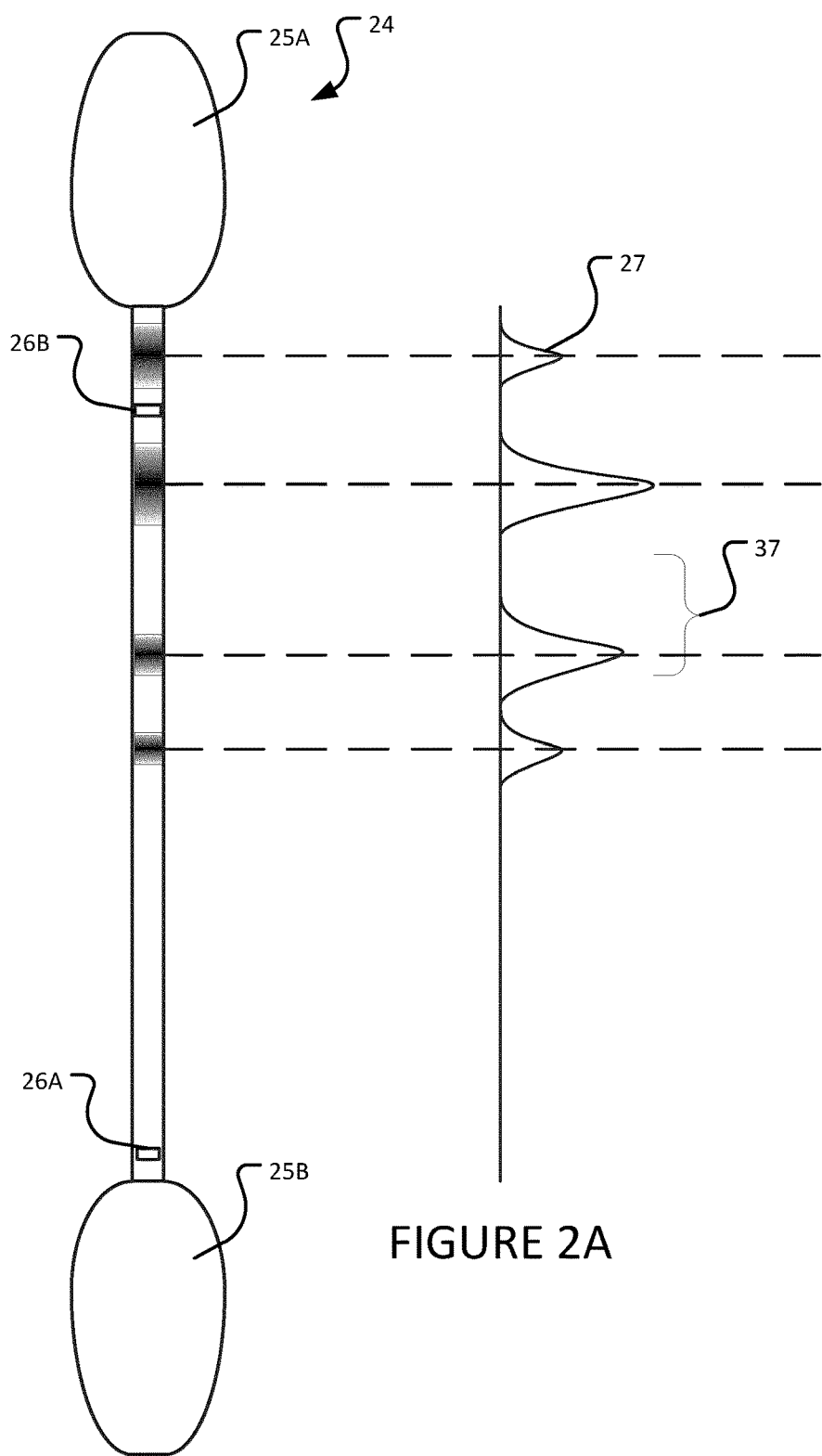
FIG. 2 illustrates schematically an image of one channel.
FIG. 2A is a plot illustrating density as a function of position along channel.

FIG. 2 illustrates schematically an image of one channel 24. Channel 24 comprises a strip 25 of a suitable electrophoresis medium with a buffer reservoir 25A, 25B at each end. A loading well 26A is located in medium 25 near buffer reservoir 25A. An extraction well is located in medium 25 at a location that is spaced apart from loading well 26A toward buffer reservoir 25B.

Also shown in FIG. 2 are various bands of DNA that have been carried along medium 25 from loading well 26A by electrophoresis. Because DNA of different sizes moves at different rates under electrophoresis, the bands at different locations represent DNA of different sizes. Different bands may have different densities in the image. The bands may all represent DNA that is present in a sample. In some embodiments DNA of a known size or a set of known sizes (e.g. a DNA ladder) may be added to the sample for the purpose of providing a size scale that may be used to determine the location of target DNA.

In some embodiments sizing references such as DNA ladders are run in the same channel 24 as input samples. This ensures sizing accuracy in comparison to embodiments where sizing references and samples are run in separate channels.

FIG. 2A is a plot illustrating density as a function of position along channel 24. Peaks in curve 27 correspond to the locations of the bands shown in FIG. 2. The methods described above may identify a peak in curve 27 corresponding to the target DNA or infer a current position of the target DNA from locations of one or more other peaks corresponding to DNA having a known size relationship(s) to the target DNA.

Some embodiments provide a scheduler. The scheduler may, for example, be implemented in software. The scheduler may schedule: the transfer of samples into source wells 26A in channels 24, commencement of electrophoresis in channels 24 and the extraction of target fractions from extraction wells 26B. In some embodiments the scheduler operates while samples are being run in channels 24 and may re-schedule extraction of target fractions in response to the monitoring of the progress of the target fraction (or a band having a known relationship to the target fraction). The schedule may initially schedule extraction of a target fraction in a time-slot that is separated from a time of commencement of electrophoresis in a channel by a period that is longer than the shortest period in which a target fraction could possibly progress from the source well 26A to the corresponding extraction well 26B. The time period used for this initial scheduling may be determined based on a measured distance from the source well 26A to the extraction well 26B in some embodiments. The time period may be generated based on an assumed average velocity of the target fraction that is less than a maximum velocity achievable within an available range of electrophoresis parameters. The assumed average velocity may be a function of a size of the target fraction and the characteristics of the medium in which electrophoresis is being performed.

In some embodiments, the length of a period scheduled by the scheduler for extraction of a target fraction is variable and depends on the sizes of nucleic acid included in the target fraction (a target fraction which includes a greater range of sizes will take longer to extract than a target fraction in which the spread of sizes is small). In some embodiments start and stop times for extraction of a target fraction are adjusted on the basis of the estimated times of arrival at the extraction well of leading and trailing edges of the target fraction.

In some embodiments the scheduler monitors for conflicts between times for extraction of target fractions from different channels 24. In some such embodiments, in the case of a conflict (i.e. periods assigned to extraction of target fractions from different channels 24 overlap the scheduler may revise the scheduled time for extraction of the target fraction from one of the channels 24 to remove the conflict. Changing of the scheduled extraction time may automatically result in parameters of the electrophoresis in the rescheduled channel 24 being altered so as to control the progress of the target fraction in the channel 24 so that the target fraction arrives at the extraction well at the rescheduled time.

In some embodiments the electrophoresis parameters for a channel 24 are controlled such that upon the leading edge of the target fraction arriving at the corresponding extraction well 26B and extraction commencing, the rate of electrophoresis is increased, thereby reducing the time over which extraction must be continued to extract the entire target fraction.

Figure 3:
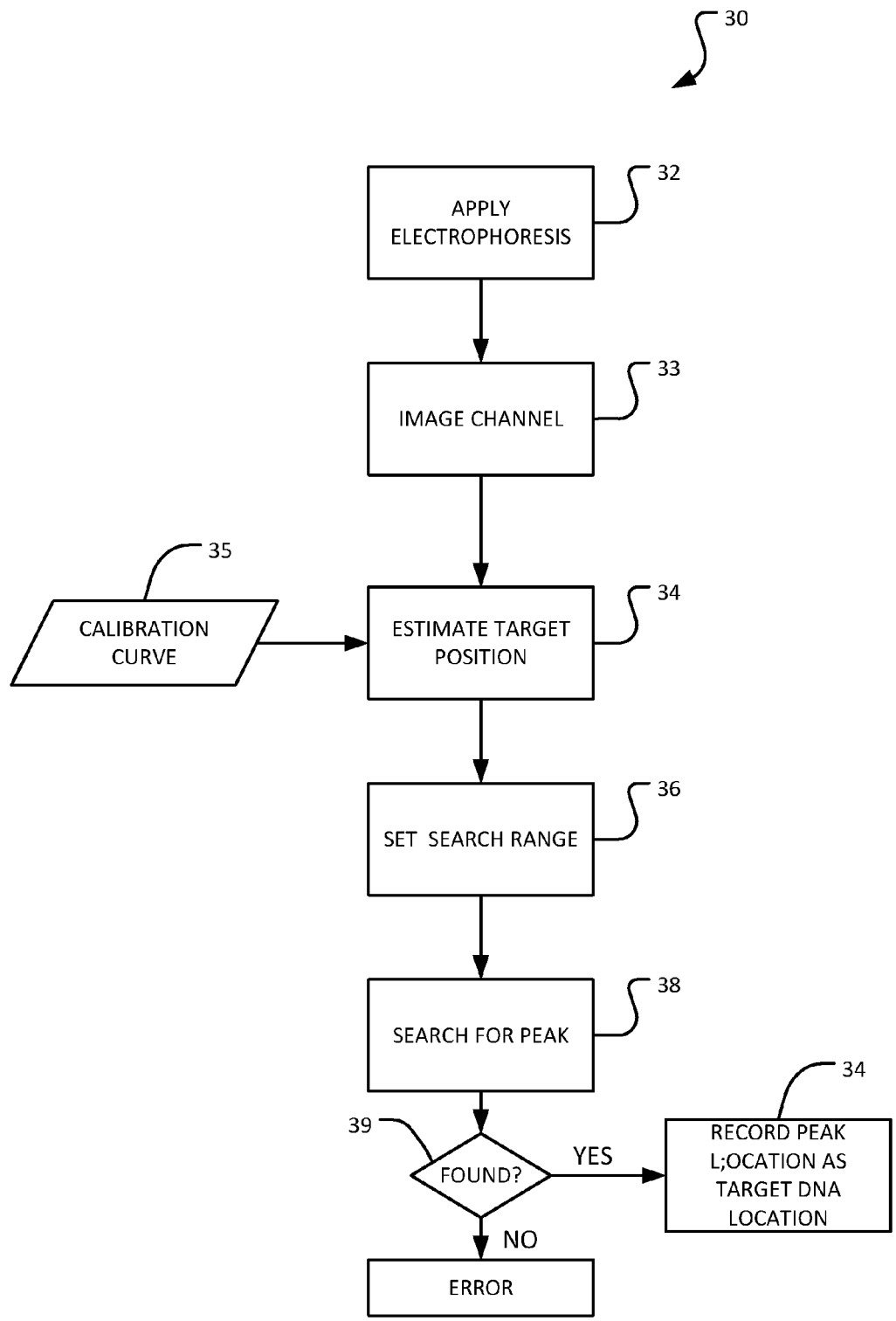
FIG. 3 illustrates a method for identifying a peak corresponding to DNA of a predetermined size.

FIG. 3 illustrates a method 30 for identifying a peak corresponding to DNA of a predetermined size in channel 24. Block 32 applies electrophoresis to a channel using known electrophoresis parameters for a period of time. Block 33 obtains an image of the channel at the end of block 33. Block 34 identifies a range of positions along the channel based upon known characteristics for the target DNA. For example, a predetermined calibration curve 35 may be provided which relates position along the channel to DNA size. In some embodiments a plurality of different calibration curves 35 are provided. The different calibration curves may apply to different media that may be used in channels 24.

Block 34 estimates a position or range of positions in which target DNA is expected to be found. The estimated position may be a function of the length of time that electrophoresis has been performed, the medium in channel 24, the electrophoresis parameters and the characteristics (especially size) of the target DNA. An operator may enter a size or size range for the target DNA. Block 34 may use an appropriate calibration curve 35 to identify the expected position of a peak in curve 27 corresponding to the target DNA. Block 36 sets a range 37 (see FIG. 2A) and searches curve 27 for a peak within range 37. If a peak is successfully detected (as determined e.g. by a YES result from block 39 then the peak is identified as the initial location of the target DNA. Once a peak corresponding to target DNA has been identified in one image the peak may be tracked through subsequent images as it propagates along the channel. Prominent features of the electropherogram profile may be identified at run-time and used to help maintain size integrity as faster-moving size references move out of the field of view.

Method 30 may be applied to identify one or more peaks corresponding to DNA in a DNA ladder and/or a sample. In some embodiments one or more peaks that are different from the target DNA are identified and tracked as described above. A current location of the target DNA may be identified relative to such peaks. For example, a user may specify the amount by which target DNA is expected to lead or lag one or more such peaks.

Figure 4:
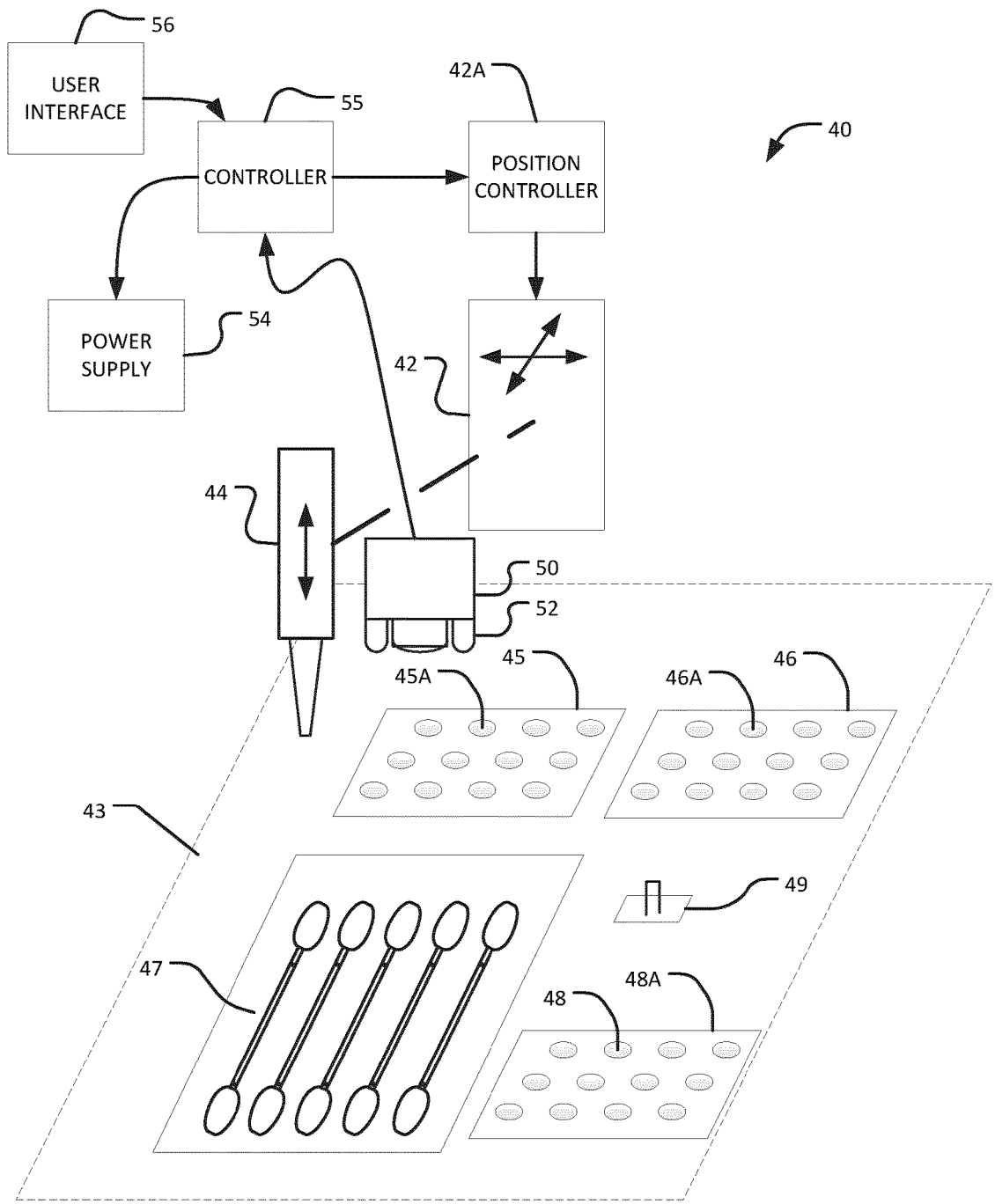
FIG. 4 illustrates apparatus according to an example embodiment.

FIG. 4 illustrates apparatus 40 according to an example embodiment. Apparatus 40 comprises a robot 42 comprising a pipetter 44 that can be positioned by robot 42 over desired locations in a field 43. For example, robot 42 may comprise an XYZ stage that supports a single-channel pipette pump, which also supports a buffer loading line and tip ejection mechanism. A source plate 45 comprises a plurality of source wells 45A. A destination plate 46 comprises a plurality of destination wells 46A. A plurality of channels 47 is provided within field 43.

Robot 42 comprises a controller 42A that can control the position of pipetter 44. Controller 42A may, for example, control robot 42 to load a channel by: picking up a pipette tip 48 at a station 48A, positioning the pipette tip over a selected source well 45A, lowering the pipette tip into the source well 45A and drawing fluid into the pipette tip 45A, raising the pipette tip and repositioning it over a loading well of a selected channel 47, lowering the pipette tip into the loading well, operating the pipetter to dispense the fluid into the source well, raising the pipette tip and moving to pipette tip to a storage area for used pipette tips and disconnecting the used pipette tip.

Controller 42A may, for example, control robot 42 to retrieve target DNA from a channel by: picking up a pipette tip 48 at station 48A, positioning the pipette tip over the extraction well in the selected channel, just prior to the estimated arrival of the target DNA lowering the pipette tip into the extraction well of the channel, drawing fluid into the pipette tip 45A over a period of time corresponding to the expected arrival of the target DNA, raising the pipette tip and repositioning it over a destination well 46A, lowering the pipette tip into the destination well, operating the pipetter to dispense the fluid into the destination well, raising the pipette tip and moving to pipette tip to a storage area for used pipette tips and disconnecting the used pipette tip.

Apparatus as described herein may be configured to process any sensible number of samples. In some embodiments, apparatus as described herein provides automated size selection for 96 samples concurrently. In other example embodiments apparatus process multiples of 96 samples concurrently. Other example embodiments are configured to process other numbers of samples.

Robots suitable for use as robot 42 are commercially available. Robots suitable for use as robot 42 may also be made from commercially-available components in ways known to those of skill in the art.

Apparatus 40 comprises an imaging device 50 which may, for example, comprise a camera arranged to obtain images of channels 47. Imaging device 50 may comprise a high dynamic range imaging device. For example, camera 50 or a controller connected to receive images from camera 50 may be configured to obtain and combine images taken at different exposure times to expand the detectable dynamic range. This allows dim bands to be visible without saturating the brightest bands.

A light source 52 illuminates channels 47 to facilitate imaging of nucleic acids propagating along the channels. Where the DNA is associated with a dye the light source may emit light corresponding to an absorption band of the dye (e.g. a band corresponding to a wavelength that excites a fluorophore of the dye. Light source 52 may comprise a filter that blocks wavelengths outside of this range. For example, SYBR Green™ dye absorbs light at 488 nm. The light source may emit blue light. For example, the light source may comprise an array of blue LEDs. Alternatively or additionally, the light source may emit UV light. Camera 50 may include a filter that preferentially admits fluorescence of the dye. for example, SYBR Green™ dye emits light at 520 nm. The camera may have a bandpass or notch filter that passes light at 520 nm but attenuates light at other wavelengths.

For example, the camera may be fixed to a component of robot 42 such that the camera is at a fixed distance from channels 47. In a prototype embodiment camera 50 and LED illuminator 52 are fixed to a Y-axis arm of robot 42.

A multi-channel electrophoresis power supply 54 is configured to provide electrophoresis potentials across channels 47. Power supply 54 may comprise a single unit or a plurality of separate units. A controller 55 is connected to receive images from camera 50 to control power supply 54 and to coordinate actions of robot 42. A user interface 56 allows users to provide control inputs and information to guide operation of apparatus 40.

In operation of an example system, source and destination plates 45, 46 are loaded along with two tip boxes containing pipette tips. Plates comprising channels 47 are set on the deck and electrode arrays are placed so that their electrodes are in electrical contact with channels 47 in the ends of the channel plate. In some embodiments the electrodes are mounted to a structure which permits them to be introduced into buffer wells at each end of each channel. For example, the apparatus may comprise a hinged frame carrying first and second electrodes corresponding to each channel. The first and second electrodes may be mounted on the hinged frame and the hinged frame may be movable between a first position wherein the first and second electrodes project into first and second buffer reservoirs of a channel and a second position wherein the first and second electrodes are removed from the first and second buffer reservoirs.

The control software is configured with the location of the samples (a whole 96 well plate or less or more), type of samples and positions of the channel plate(s).

When a run commences, buffer wells in the channel plates are filled. The samples are loaded sequentially (e.g. by the robot into the loading wells in channels 47) and electrophoresis commences. In one embodiment, the on board camera 50 is used to locate the extraction well in each channel 47 avoiding the requirement to manually configure the location of the extraction wells. This facilitates the possibility of providing extraction wells at different locations within their channels 47.

Some embodiments comprise a mechanism for measuring and/or setting the Y position of the pipette tip. Knowing the exact position of the pipette tip facilitates precise loading and retrieval of nucleic acid samples in small wells. Such a mechanism is useful because the ends of different pipette tips can be at somewhat different locations relative to the robot when mounted to the pipetter. In an example embodiment the mechanism comprises a switch (which can be for example a microswitch, proximity switch or the like) that changes state when a pipette tip is in a predetermined location relative to the switch. The switch may be at a convenient location in the field of the robot.

In some embodiments, the switch is located near a supply of fresh pipette tips such that the Y position of each new pipette tip may be set by moving the robot to bring the pipette tip against the switch. In such embodiments the pipette tip may be positioned near to the switch and then moved toward the switch in the Y direction until the switch changes state. This mechanism may be used to individually measure the location of the end of each pipette tip after a tip is loaded. The measured location may be used to compensate for slight misalignments in different pipette tips. The illustrated system 40 comprises a switch 49 arranged to switch when a pipette tip presses against the switch in a Y direction (a direction parallel to channels 47).

Figure 5:
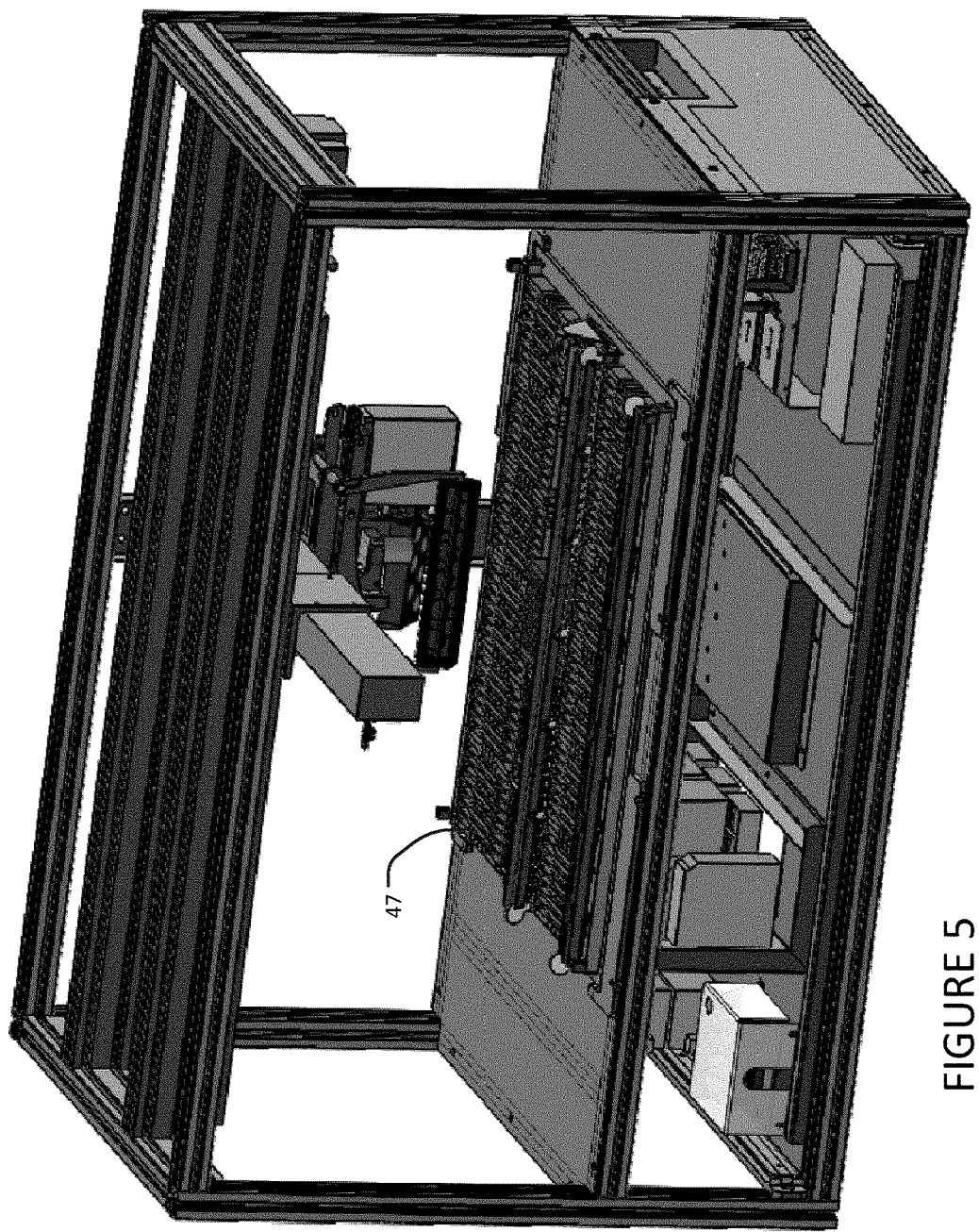
FIG. 5 shows an example robot.

FIG. 5 shows an example robot. FIG. 5 shows a lower deck which accommodates controllers and power supplies, and an upper deck which accommodates channel plates and electrodes. Above that is the pipetting head with pump, buffer delivery system and camera and lights for imaging the channels.

Figure 5A:
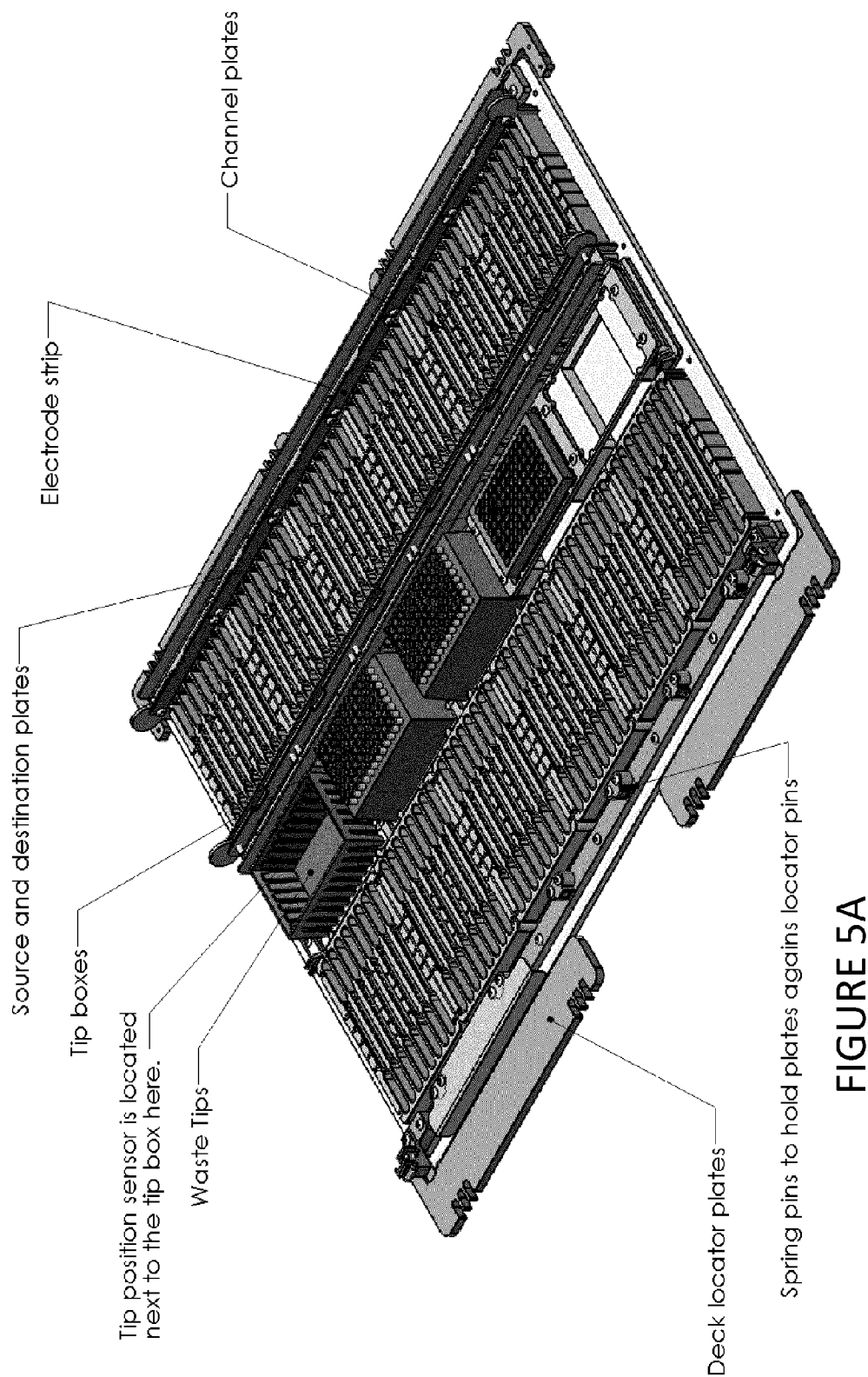
FIG. 5A shows an example deck.

FIG. 5A shows an example deck. FIG. 5A shows deck locator plates that hold the deck in position. Tip boxes, source places, destination plates and channel plates are all mounted to the deck. At least the source places, destination plates and channel plates are removable from the deck. Spring pins are provided to hold the plates against locator pins so that source wells, destination wells and channels will be in known positions when the plates are installed on the deck.

Figure 5B:
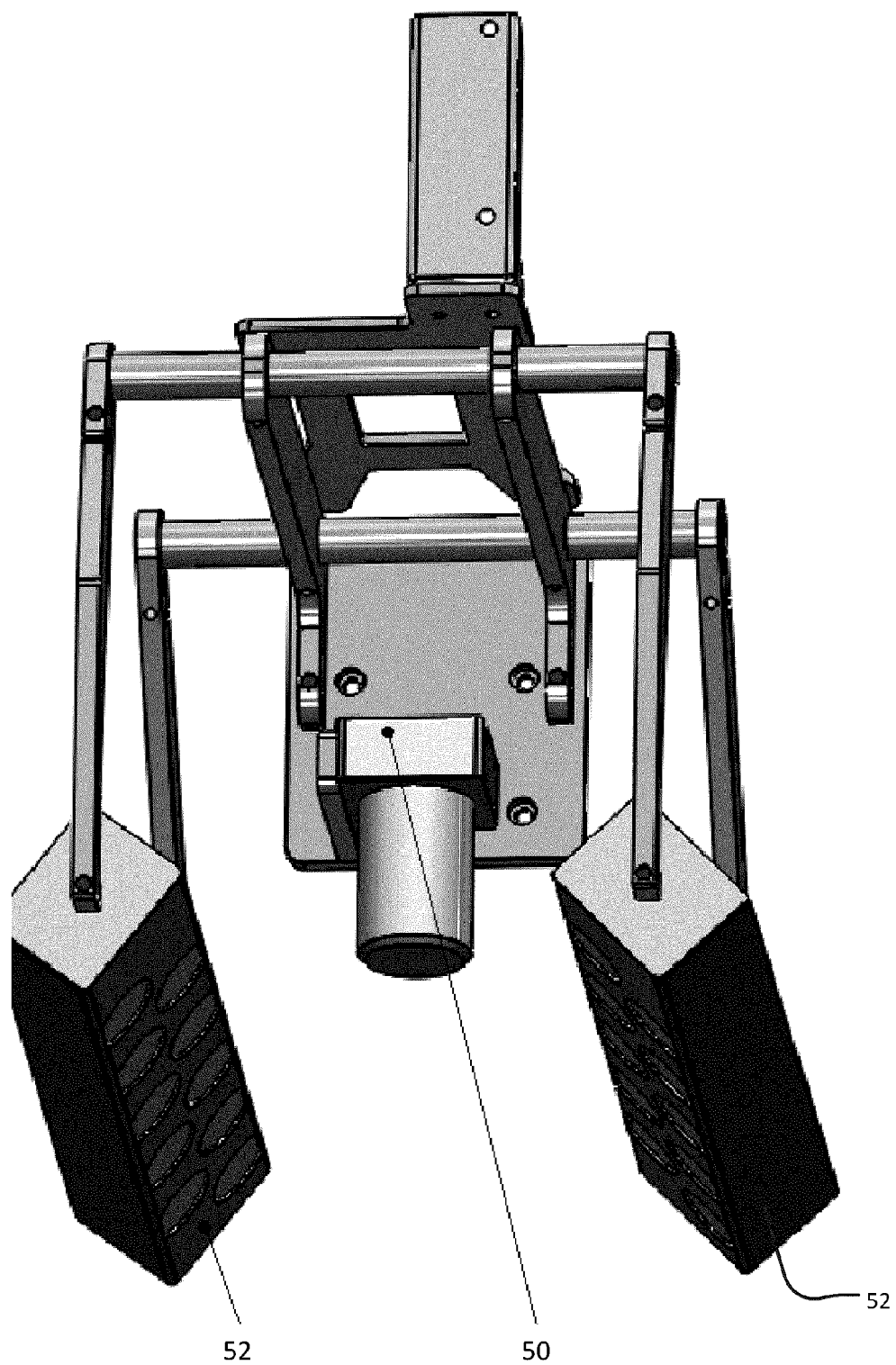
FIG. 5B shows an example camera assembly.

FIG. 5B shows an example camera system comprising a camera 50 and LED arrays 52. LED arrays 52 comprise blue light emitting light sources such as blue LEDs of LEDs covered by blue filters in some embodiments.

In an example embodiment, controller 55 comprises a processor configured to execute instructions provided in software. The software creates a run protocol (which sample runs in which channels, in which order, and what destination wells the respective extractions will end up in) based on data input by the user. This is communicated to the user graphically.

Figure 6:
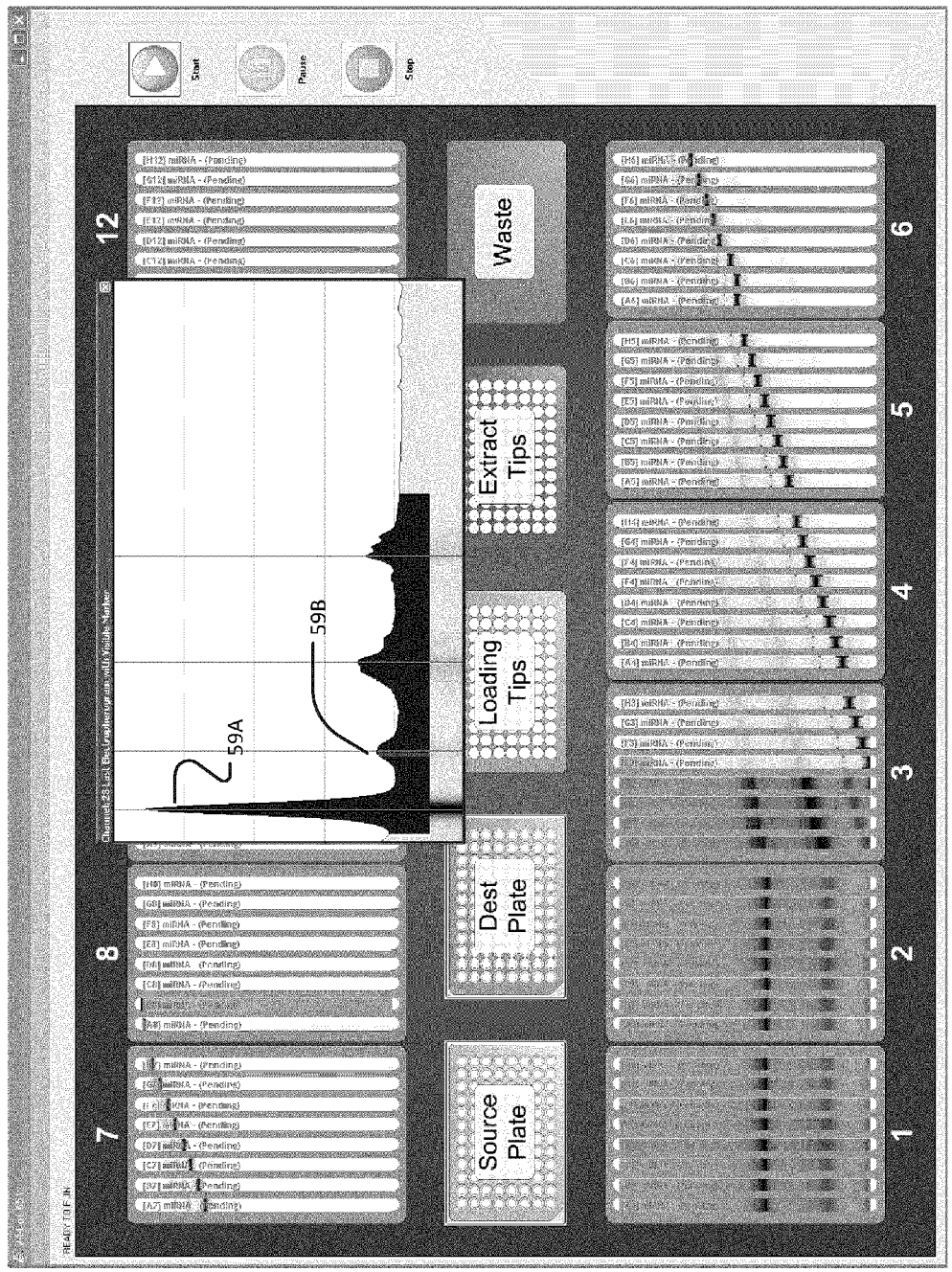
FIG. 6 is a screen shot of an example graphical display.

FIG. 6 is a screen shot of an example graphical display. FIG. 6 shows the display mid-run. Samples have been loaded sequentially starting in the lower left and the first two and half plates have completed runs. The remaining samples to the right are running and each channel's status is shown graphically based on the most recent image. The plot at top is an electropherogram for a channel selected by the user, showing a size reference peak 59A and target region 59B.

Another aspect of the invention that may be used together with a robot as described above but also may have other applications provides channel plates for use in separation of nucleic acids. In some embodiments one or more channels is provided on a plate. The plate may be removably placed within the field of a robot as described above, for example. Providing DNA separation media in channels as opposed to slabs (e.g. slab gels) has the advantage that the possibility of cross-contamination from one sample to another is reduced.

Figure 7B:
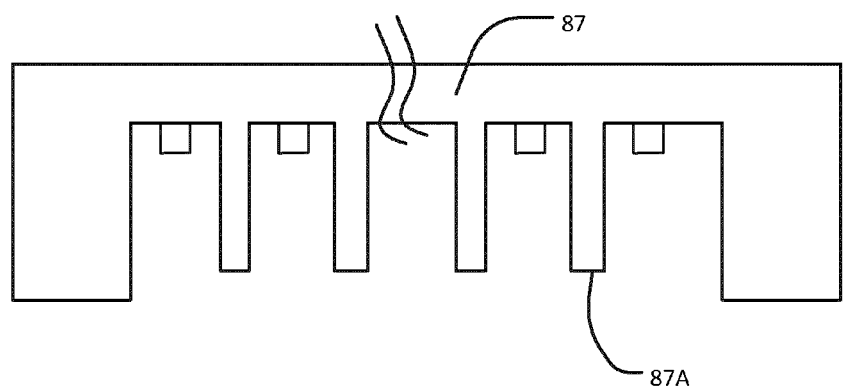
FIG. 7B shows an example comb useful for forming loading or extraction wells.
Figure 7C:
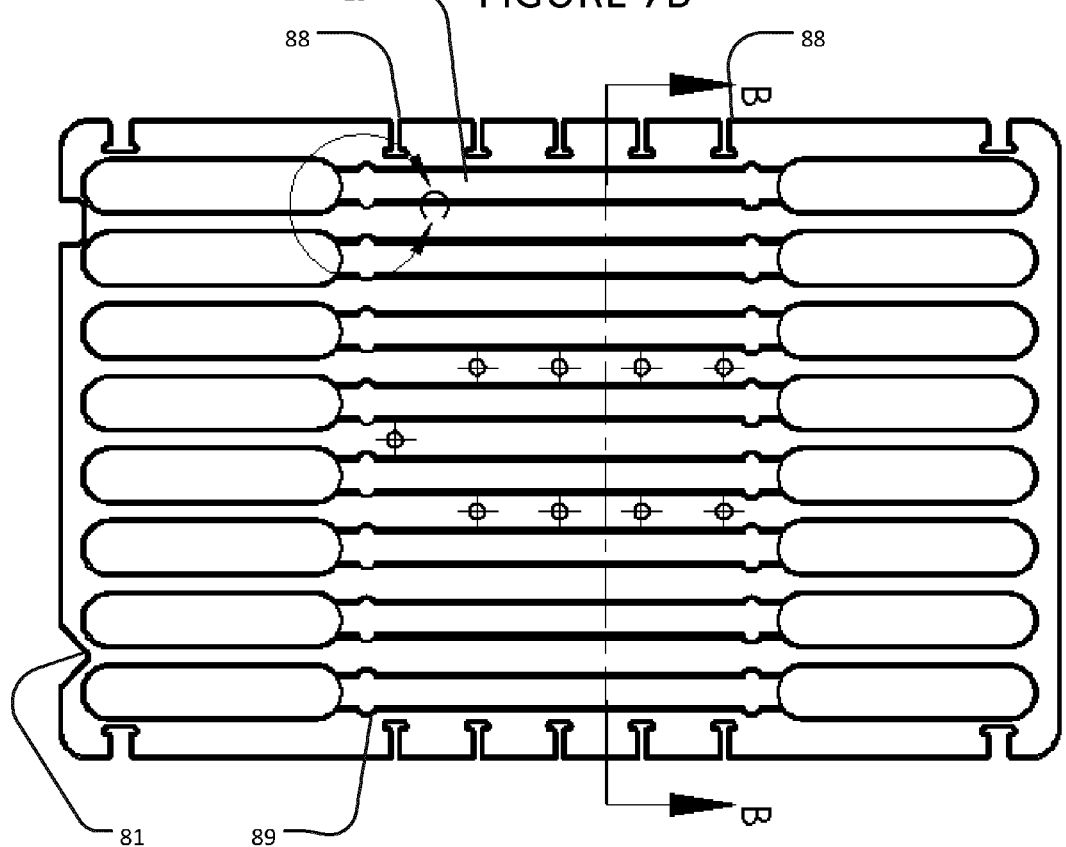
FIG. 7C is a plan view of an example channel plate according to another embodiment.

FIG. 7 is a plan view of an example channel plate 80. Plate 80 comprises location features 81 such as holes (see FIG. 7A) or notches (see FIG. 7C) for receiving locating pins or other locating features that permit plate 80 to be repeatably positioned in the field of a robot or other apparatus. A plurality of channels 24 extend along plate 80. Each channel 24 comprises a strip 25 of a suitable electrophoresis medium. A buffer reservoir 25A, 25B is provided at each end of strip 25. A loading well 26A is located in strip 25 near buffer reservoir 25A. An extraction well 26B is located in strip 25 at a location that is spaced apart from loading well 26A toward buffer reservoir 25B. In some applications extraction wells 26B of different channels are aligned with one another but this is not mandatory. In some applications it may be convenient to provide extraction wells 26B that are at different locations along strip 25 in different channels 24.

FIG. 7A is a cross section of an individual channel 24. Channel 24 optionally has a small step edge on either side of strip 25. In the illustrated embodiment steps 83 are shown. Steps 83 provide corners 84. Corners 84 run length-wise along strip 25 parallel to one another. In the illustrated embodiment, corners 84 are parallel to flat top and bottom surfaces 84A and 84B of plate 80. Medium 86 (for example an agarose gel, an acrylamide gel or the like) fills strip 25 up to the level of corners 84. Steps 83 help to make the top surface of material 86 in strip 85 flat along the length of strip 25. The presence of corners 84 as material 86 is introduced into strip 25 helps to reduce the tendency of surface tension of material 86 to form a meniscus at the surface of material 86. Optional features such as small divots or dimples 89 (See FIG. 7C) may be formed in walls of strip 25 near the ends of strip 25 in order to mechanically lock material 86 in place.

Dimensions of channel 24 may be varied. In an example embodiment, strip 25 has a depth in the range of about 6 to 12 mm, preferably 8 to 10 mm. In an example embodiment, strip 25 has a width of 3 mm to 11 mm, preferably 4 mm to 7 mm. The principles described herein may be applied, however, to channels of other dimensions.

Plate 80 may be made of a suitable plastic or other electrically-insulating material. In some embodiments plate 80 is injection molded however, plate 80 may also be fabricated by machining or in any other suitable manner.

A plate 80 may be prepared by temporarily damming or filling buffer reservoirs 25A and 25B and pouring a suitable amount of a settable material 86 into strips 25. Preferably the entire volume of each buffer reservoir is filled while material 86 is cast so that material 86 is unable to flow into the buffer reservoirs. For example, an agarose gel may be poured into strips 25 while the gel is in a liquid form and then allowed to set in strips 25. The amount of material 86 introduced into each strip may be just enough that a surface of the material is at the level of corners 84.

Loading and extraction wells may be formed in material 86 while the material is being cast into strips 25. In other embodiments the loading and/or extraction wells may be formed after material 86 has set. In some embodiments loading and/or extraction wells are formed by placing loading and/or extraction combs at appropriate locations along strips 25. FIG. 7B shows an example comb 87. Each comb 87 comprises a row of pins 87A. A comb 87 may be placed on plate 80 transversely to strips 25 such that pins 87A are arranged to project into strips 25 of the channels 24 crossed by the comb 87.

Plate 80 may comprise locating features 88 to place combs 87 in desired alignment for forming loading wells and/or extraction wells. Multiple sets of locating features 88 may be provided to facilitate forming extraction wells at different locations along strips 25. As noted above, it can be desirable to provide extraction wells at a location that is tailored to the separation to be performed. The best length of separation channel between loading well 26A and extraction well 26B depends on the length of DNA or other target nucleic acid and the desired degree of separation.

A comb 87 for forming extraction wells may have pins 87A that are somewhat wider than the pins 87A used to form loading wells. Providing loading wells 26A that do not extend the full width of strips 25 helps to avoid loss of sample at the sides of a loading well. Extraction wells 26B may extend the full width of strips 25 or nearly the full width of strips 25.

A range of embodiments provide channels in which loading wells are wider than extraction wells. In one particular example embodiment, the loading well has a dimension of 1.2×3.5×9 mm, and the extraction well has a dimension of 1.2×5.5×9 mm (i.e., 2 mm wider than the loading well). A loading well having a dimension of 1.2×3.5×9 mm allows a sample having a volume of up to 37.8 µl to be loaded. An extraction well having a dimension of 1.2×5.5×9 mm allows a volume of up to 59.4 µl to be withdrawn.

Combs 87 may be designed so that pins 87A that form the wells can 'float' slightly (e.g. about 0.25 mm) in their mounting frames. This facilitates removing combs 87 after material 86 has set.

A plate 80 comprising one or more channels 24 may be provided in the form of a pre-prepared cassette provided in sterile packaging. The packaging may, for example, comprise a sterile cover that can be peeled off to reveal channels 24. In some embodiments the cassette may be supplied with combs inserted into the loading and/or extraction wells. A user may remove the combs prior to use.

FIG. 7C is a plan view of an example channel plate according to another embodiment.

Figure 7D:
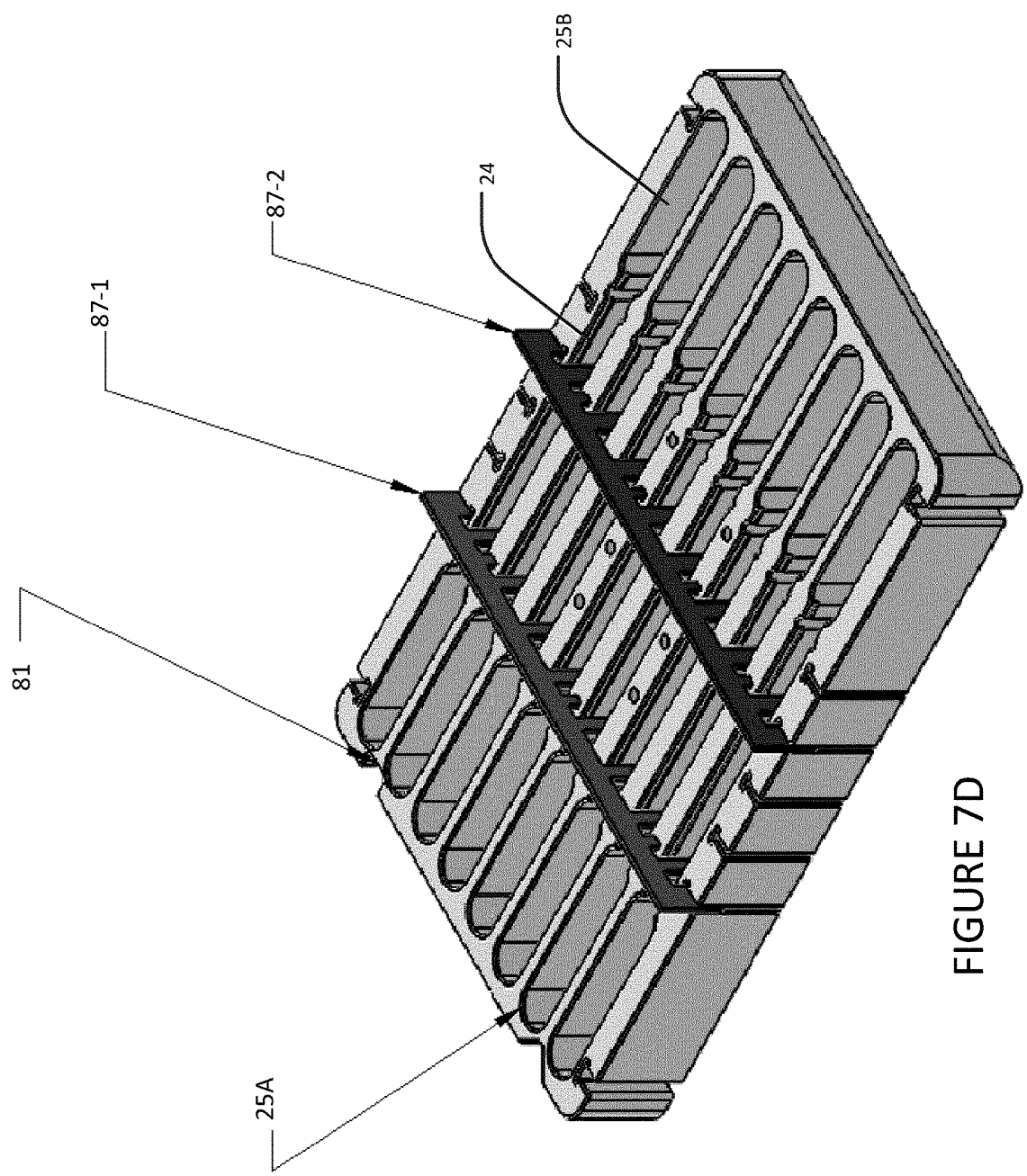
FIG. 7D is a perspective view of a channel plate with combs engaged for forming source and extraction wells.

FIG. 7D is a perspective view of a channel plate with combs 87-1 and 87-2 inserted in preparation for casting an electrophoresis medium into channels 24. Comb 87-1 may have narrower pins than comb 87-2 in some embodiments.

although a camera provides a convenient tool for imaging a plurality of channels and simultaneously tracking progress of one or more reference fractions in each of the channels, other tools may be used in place of a camera. For example, a 1-D line scanner could be provided to measure a concentration of a nucleic acid as a function of position along a channel. Further, it is not mandatory that the camera view the channels from above. In some embodiments trays carrying the channels are transparent, at least in their parts underlying the channels and the camera views the channels from below through the plates.

Interpretation of Terms

Unless the context clearly requires otherwise, throughout the description and the claims:
"comprise," "comprising," and the like are to be construed in an inclusive sense, as opposed to an exclusive or exhaustive sense; that is to say, in the sense of "including, but not limited to".
"connected," "coupled," or any variant thereof, means any connection or coupling, either direct or indirect, between two or more elements; the coupling or connection between the elements can be physical, logical, or a combination thereof.
"herein," "above," "below," and words of similar import, when used to describe this specification shall refer to this specification as a whole and not to any particular portions of this specification.
"or," in reference to a list of two or more items, covers all of the following interpretations of the word: any of the items in the list, all of the items in the list, and any combination of the items in the list.
the singular forms "a", "an" and "the" also include the meaning of any appropriate plural forms.
Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise 'firmware') capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs") and the like. Examples of configurable hardware are: one or more programmable logic devices such as programmable array logic ("PALs"), programmable logic arrays ("PLAs") and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times. In addition, while elements are at times shown as being performed sequentially, they may instead be performed simultaneously or in different sequences.

Software and other modules may reside on servers, workstations, personal computers, embedded processors, process controllers, tablet computers, and other devices suitable for the purposes described herein.

The invention may also be provided in the form of a program product. The program product may comprise any non-transitory medium which carries a set of computer-readable instructions which, when executed by a data processor, cause the data processor to execute a method of the invention. For example, the computer readable instructions may program a computer to control a robotic nucleic acid sizing system as described herein and/or to schedule operations in a nucleic acid sizing system as described herein. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions and sub-combinations as may reasonably be inferred. The scope of the claims should not be limited by the preferred embodiments set forth in the examples, but should be given the broadest interpretation consistent with the description as a whole.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations.

What is claimed is:

1. A method for size-selection of nucleic acids, the method comprising:
    loading a sample comprising nucleic acids into a channel, wherein the nucleic acids comprise a reference fraction and target fraction and wherein the nucleic acids of the reference fraction and the nucleic acids of the target fraction have different sizes;
    moving the sample along the channel by electrophoresis;
    automatically monitoring progress of the reference fraction along the channel, wherein the monitoring comprises, at spaced apart times, obtaining images of the channel and identifying areas in the images corresponding to the reference fraction;
    based on the monitoring of the reference fraction, estimating a time of arrival of the target fraction of the nucleic acids at an extraction well in the channel, wherein the estimated time of arrival of the target fraction is based on an average velocity of the target fraction based on differences between positions of the reference fraction in two or more of the images; and
    extracting fluid containing the target fraction from the extraction well at the estimated time of arrival.

2. A method according to claim 1 wherein estimating the time of arrival of the target fraction comprises estimating a difference between an estimated arrival time of the reference fraction at the extraction well and the estimated arrival time of the target fraction at the extraction well.

3. A method according to claim 1 wherein estimating the time of arrival of the target fraction comprises determining an average velocity of the target fraction based on differences between the positions of the reference fraction in two or more of the images.

4. A method according to claim 1 comprising, prior to moving the nucleic acids along the channel combining the nucleic acids with a dye.

5. A method according to claim 4 wherein the dye comprises a fluorophore or a chromophore.

6. A method according to claim 4 wherein obtaining each of the images comprises operating an imaging device to obtain a plurality of different exposures of the channel and combining the plurality of different exposures to yield the image, wherein the image has a greater dynamic range than any of the plurality of different exposures.

7. A method according to claim 4 comprising illuminating the channel with visible light or UV light while obtaining the images.

8. A method according to claim 7 wherein the visible light or the UV light comprises a wavelength that corresponds to an absorption band of the dye.

9. A method according to claim 1 wherein the method is performed in parallel to process a plurality of samples in a plurality of channels, the method further comprising scheduling a time of arrival for the target fraction at the extraction well of each of the channels; comparing the scheduled time of arrival to the estimated time of arrival and adjusting one or more electrophoresis parameters of an electrophoresis signal based on any difference between the scheduled time of arrival and the estimated time of arrival such that the estimated time of arrival of the target fractions for each of the plurality of the channels is the same.

10. A method according to claim 9 wherein adjusting the one or more electrophoresis parameters comprises adjusting a duty cycle of the electrophoresis signal.

11. A method according to claim 9 wherein adjusting the one or more electrophoresis parameters comprises adjusting a potential of the electrophoresis signal.

12. A method according to claim 9 comprising controlling a rate of movement of the nucleic acids along the channel by proportional feedback control of the one or more electrophoresis parameters based on an error signal comprising a difference between the scheduled time of arrival and the estimated time of arrival.

13. A method according to claim 9 comprising reducing a difference between the estimated arrival time and the scheduled arrival time by temporarily interrupting application of an electrophoresis signal to the channel.

14. A method according to claim 1 comprising determining a location of the extraction well in the channel by image analysis.

15. A method according to claim 14 wherein estimating the time of arrival of the target fraction of the nucleic acids at the extraction well is based in part on the location of the extraction well as determined by the image analysis.

16. A method according to claim 1 wherein extracting fluid containing the target fraction from the extraction well is performed over a period determined automatically from a range of sizes of nucleic acid included in the target fraction.

17. A method according to claim 16 comprising estimating times of arrival at the extraction well of leading and trailing edges of the target fraction and adjusting start and stop times for extraction of the target fraction on the basis of the estimated times of arrival at the extraction well of the leading and trailing edges of the target fraction.

18. A method according to claim 17 comprising automatically controlling the electrophoresis for the channel such that upon the leading edge of the target fraction arriving at the extraction well, the rate of electrophoresis is increased.

19. A method according to claim 9 wherein the electrophoresis parameters of each of the plurality of channels are independently controlled.

20. A method according to claim 9 further comprising operating a robotic system comprising a pipetter to transfer the plurality of samples into the plurality of channels.

21. A method according to claim 20 wherein extracting the fluid containing the target fraction from the extraction well comprises operating the robotic system to place a pipette tip into the extraction well, operating the pipetter to withdraw the fluid from the extraction well and operating the robotic system to transfer the removed fluid to a destination well.

22. A method according to claim 1 wherein the method is performed in parallel to process a plurality of samples in a plurality of channels the method further comprising scheduling a time of arrival for the target fraction at the extraction well; comparing the scheduled time of arrival to the estimated time of arrival and adjusting one or more electrophoresis parameters of an electrophoresis signal based on any difference between the scheduled time of arrival and the estimated time of arrival: comprising automatically controlling the moving of the nucleic acids in first and second ones of the channels such that the estimated time of arrival of the target fraction for the first channel is different from the estimated time of arrival of the target fraction for the second channel.

23. A method according to claim 20 wherein the pipetter comprises a multichannel pipetter and extracting the fluid containing the target fraction from the extraction well is performed simultaneously for a plurality of the channels by operating the robotic system to place pipette tips for the channels of the multichannel pipetter into the extraction wells of a corresponding plurality of the channels, operating the pipetter to withdraw the fluid from the extraction wells and operating the robotic system to transfer the removed fluid to a corresponding plurality of destination wells.

24. A method according to claim 9 wherein the target fractions for the plurality of channels comprise a plurality of different target fractions.

25. A method according to claim 1 wherein the target fraction of the nucleic acid comprises an adapter joined to a nucleic acid molecule of interest, and the reference fraction of the nucleic acids comprise the adapter which is not joined to the nucleic acid molecule of interest.

26. A method according to claim 1 wherein the monitoring comprises automatically monitoring progress of a plurality of reference fractions of the nucleic acids along the channel wherein the reference fraction is one of the plurality of reference fractions of the nucleic acids.

27. A method according to claim 26 wherein said plurality of reference fractions of the nucleic acids comprise a DNA or RNA ladder of known sizes.

28. A method according to claim 1 comprising specifying a size or size range of the target fraction of the nucleic acids.

29. A method according to claim 1 wherein the nucleic acids comprise at least a first target fraction and a second target fraction, and the estimating and extracting steps comprise:
    estimating a time of arrival of the first target fraction at the extraction well in the channel;
    extracting fluid containing the first target fraction from the extraction well at the estimated time of arrival of the first target fraction;
    continuing electrophoresis in the channel;
    estimating a time of arrival of the second target fraction at the extraction well in the channel; and
    extracting fluid containing the second target fraction from the extraction well at the estimated time of arrival of the second target fraction.

30. A method according to claim 29 comprising transferring the fluid containing the first target fraction and the fluid containing the second target fraction to separate destination wells.

31. A method according to claim 29 comprising transferring the fluid containing the first target fraction and the fluid containing the second target fraction to the same destination well.

32. A method according to claim 29 comprising scheduling a first scheduled time for extracting the first target fraction, and scheduling a second scheduled time for extracting the second target fraction.

33. A method according to claim 32 comprising controlling one or more electrophoresis parameters for the channel to bring the first target fraction to the extraction well at the first scheduled time.

34. A method according to claim 32 comprising controlling one or more electrophoresis parameters for the channel to bring the second target fraction to the extraction well at the second scheduled time after the first target fraction has been extracted.

35. A method according to claim 29 wherein the nucleic acids comprise a plurality of target fractions and the plurality of target fractions are extracted from the extraction well of the channel at a plurality of different times.

36. A method according to claim 9 wherein the nucleic acids in each one of the plurality of channels comprise a plurality of target fractions and the plurality of target fractions in each one of the channels are extracted from the extraction well at a plurality of times.

37. A method according to claim 36 comprising controlling one or more electrophoresis parameters for the channels to bring first target fractions of the plurality of target fractions of the plurality of channels to the extraction wells at a common first scheduled time.

38. A method according to claim 37 wherein the nucleic acids in each one of the plurality of channels comprise a plurality of target fractions and the plurality of target fractions in each one of the channels are extracted from the extraction well at a plurality of times, the method further comprising controlling one or more electrophoresis parameters for the channels to bring first target fractions of the plurality of target fractions of the plurality of channels to the extraction wells at different times.

39. A method according to claim 37 comprising controlling one or more electrophoresis parameters for the channels to bring second target fractions of the plurality of target fractions of the plurality of channels to the extraction wells at a common second scheduled time.

40. A method according to claim 38 comprising controlling one or more electrophoresis parameters for the channels to bring second target fractions of the plurality of target fractions of the plurality of channels to the extraction wells at different times.

* * * * *